United States Patent [19]

Elseviers et al.

[11] Patent Number: 5,831,078
[45] Date of Patent: Nov. 3, 1998

[54] PROCESS FOR THE PRODUCTION OF ARABINITOL

[75] Inventors: Myriam Elseviers, Kampenhout; Hilde Odile Jozefine Lemmens, Kontich; Sonia Marianne Jeannine Coomans, Vilvoorde; Harald Wilhelm Walter Röper, Brussels, all of Belgium

[73] Assignee: Cerestar Holding B.V., Sas van Gent, Netherlands

[21] Appl. No.: 898,928

[22] Filed: Jul. 23, 1997

[30] Foreign Application Priority Data

Jul. 25, 1996 [GB] United Kingdom ............... 9615635

[51] Int. Cl.$^6$ ............................... C07H 1/00; C07C 27/04
[52] U.S. Cl. ...................... 536/124; 536/18.5; 536/121; 568/852; 568/854; 568/861; 568/864
[58] Field of Search ............................... 514/62; 536/29.1, 536/121, 124, 18.5; 568/852, 854, 861, 864

[56] References Cited

U.S. PATENT DOCUMENTS 4,125,559 11/1978 Scholz et al. ........................ 562/531
5,563,303 10/1996 Vuorinen ........................... 568/864

FOREIGN PATENT DOCUMENTS

| 716066 | 6/1996 | European Pat. Off. . |
| 716067 | 6/1996 | European Pat. Off. . |
| 618 164 | 9/1935 | Germany . |
| 620 248 | 9/1935 | Germany . |
| 1 580 665 | 12/1980 | United Kingdom . |
| 93/19030 | 9/1993 | WIPO . |
| 9319030 | 9/1993 | WIPO . |

*Primary Examiner*—Marian C. Knode
*Assistant Examiner*—Howard C. Lee
*Attorney, Agent, or Firm*—Pillsbury, Madison Sutro LLP; Cushman Darby & Cushman IP Group

[57] ABSTRACT

A method is disclosed for producing a pentitol. The disclosed method more particularly relates to producing arabinitol from hexoses, e.g. galactose and/or glucose, and/or fructose, or lactose hydrolysate, or invert sugar, or starch hydrolysates. The hexose is oxidatively decarboxylated to a $C_5$-aldonic acid which is thereafter catalytically hydrogenated to obtain the desired arabinitol.

15 Claims, 7 Drawing Sheets

PROCESS FOR THE PRODUCTION OF ARABINITOL

TECHNICAL FIELD

The present invention discloses a method for producing a pentitol. The present invention relates to a method for producing arabinitol from hexoses, e.g galactose and/or glucose, and/or fructose, or lactose hydrolysate, or invert sugar, or starch hydrolysates. The hexose is oxidatively decarboxylated to a $C_5$-aldonic acid followed by catalytic hydrogenation.

BACKGROUND OF THE INVENTION

Chemical conversion of hexoses leading to arabinitol has been extensively studied. Andrews et al. J. Org. Chem. (1989) 54 5257–5264 describe such a chemical process i.e. the decarbonylation of aldose sugars by chlorotris-(triphenylphosphine) rhodium(I). Unprotected $C_n$ aldose sugars are decarbonylated by one equivalent of chlorotris-(triphenylphosphine)rhodium(I) to give the corresponding $C_{n-1}$ alditol. According to the authors it has not been possible to perform these reactions under catalytic conditions. Large scale application of this method, involving the use of large amounts of rhodium is not feasible. Application of these decarbonylation reactions is further limited by the solvents required. The preferred solvents are polar enough to dissolve the sugar, however, they should be sufficiently non-coordinating to permit the metal complexes to function effectively. These characteristics have limited the solvents which can be used with the known metal complexes. The problems described with the application of the method disclosed in the article of Andrews et al. (cited above) have to a certain extent been overcome as described in the co-pending patent application EP 0 716 066.

Lignocellulosic materials such as arabinans and arabinogalactans are also used as starting materials. These materials can be hydrolyzed to give the corresponding monosaccharides, e.g. L-arabinose which can be further hydrogenated to the corresponding polyols by using known technology. The hydrolysis suffers however from the same disadvantages as the hydrolysis process to produce xylose from xylan containing materials i.e. low yield and low product purity are the main drawbacks of these processes.

An alternative synthesis of D-arabinose consists in the oxidative degradation of gluconic acid, extensively described by Ruff in Berichte der Deutschen Chemischen Gesellschaft 32 (1899) 553–554. However, starting from glucose a minimum of three reaction steps are required to obtain arabinitol.

Oxidative decarboxylation is a well known process and has been applied for the oxidative degradation of monosaccharides as well as disaccharides, such as lactose, maltose and cellobiose. The basic principle has been demonstrated by Spengler and Pfannenstiel Z. Wirtschafts-gruppe Zuckerindustrie, Tech. Tl. 1935, 85, 546–552, and DE 620 248. To increase the selectivity of the reaction preferably oxygen gas is used instead of air. DE 1 044 793 describes a selectivity of 73% by applying air, the selectivity increases to 78% by applying oxygen gas. This is further demonstrated in the patent application DE 618 164.

It is of course interesting to obtain a high selectivity for this type of reactions. To obtain high selectivities either the reactions are performed under high pressure, additionally redox catalysts are added to the reaction medium, or organic solvents are added to improve oxygen transfer. Anthraquinone-2-sulphonic acid (AMS) has been described by Vuorinen T. et al Starch 1991 43 194–198, as an efficient redox system to assist during the oxidative decarboxylation, generally hydrogen peroxide is added to re-oxidize the anthraquinone derivative. However, even in the presence of anthraquinone-2-sulphonic acid, still 6 bar oxygen pressure is required to obtain a good conversion. Omitting AMS requires the increase of the oxygen pressure to at least 11 bar and preferably to 26 bar to increase the selectivity (Scholtz et al. U.S. Pat. No. 4,125,559). Moreover, organic solvents such as methanol are added to the reaction medium to improve the oxygen transfer.

According to FR 2 722 200 it is possible to substitute oxygen gas by air and work at atmospheric pressure, but the addition of AMS and hydrogen peroxide is then a necessity. The addition of methylene blue is described in U.S. Pat. No. 2,587,906 to increase the selectivity of the oxidative degradation, but removal of this additive is as difficult as the removal of anthraquinone-2-sulphonate (AMS).

The reaction in the presence of AMS requires an extensive working-up procedure to remove completely AMS from the substrate. FR 2 722 200 mentions the treatment with granular active carbon, but without explaining the procedure nor the results obtained.

There exists a need for an economically valuable method of producing arabinitol in high yield, comprising reaction steps which are giving intermediates with a low level of impurities (e.g. good selectivity of the reaction), and which do not require extensive purification (e.g. which might be needed due to the addition of reagents which are not easily removed from the final product). Preferably such reactions should start from readily available substrates i.e. hexoses and should be performed at low pressure i.e. below about 6 bar and in the absence of AMS or another substance which is difficult to remove. The present invention provides such a method.

SUMMARY OF THE INVENTION

The present invention relates to a method for producing a pentitol, i.e. D-arabinitol from a hexose characterized in that the method comprises oxidative decarboxylation followed by catalytic hydrogenation, preferably the method comprises the following steps:

a) oxidative decarboxylation of a hexose to yield a $C_5$-intermediate consisting mainly of an alkali metal aldonate, b) crystallization of the alkali metal $C_5$-aldonate, c) protonation of the alkali metal salt to the corresponding free acid, d) optionally crystallization of the $C_5$-aldonolactone, and e) hydrogenation of the aldonic acid (lactone) to the corresponding pentitol.

The starting material is a hexose such as glucose (anhydrous, monohydrate), high dextrose syrups (starch hydrolysates)), and/or galactose, invert sugar, or lactose hydrolysate.

In a preferred embodiment of the present invention the hexose is glucose and the product is arabinitol.

The oxidative decarboxylation is performed at an oxygen pressure between 0.5 and 10 bar, preferably between 1 and 6 bar, more preferably between 2 and 5 bar. The reaction is performed in the absence of anthraquinone derivatives and without the addition of organic solvents.

The product of the oxidative decarboxylation can be hydrogenated without extensive purification.

The method of the present invention is characterised in that step a) is an oxidative decarboxylation reaction without addition of anthraquinone derivatives and without the addition of organic solvents, at low oxygen pressure, and optional addition of hydrogen peroxide.

The crystallization step is performed directly from water or from water/alcohol mixtures, preferably from water.

The protonation is performed by using ion exchange resins, preferably strong ion exchange resins (cation exchange).

It is a further part of the present invention that the hydrogenation is performed in the presence of a hydrogenation catalysts, preferably a ruthenium based catalyst with a temperature for the hydrogenation between 100° and 170° C., preferably between 110° and 150° C., more preferably between 120° and 140° C. The hydrogenation is promoted by the addition of acids, preferably phosphoric acid or boric acid.

DETAILED DESCRIPTION OF THE INVENTION

Basically, the method of the present invention demonstrates that it is possible to perform oxidative decarboxylation of a hexose at low pressure in the absence of AMS and with retention of selectivity. The absence of AMS makes it possible to perform a catalytic hydrogenation on the product without requiring extensive purification.

The present invention can be summarised as follows. The invention discloses the oxidative decarboxylation of $C_6$-carbohydrates to alkali metal $C_5$-aldonates. The oxidative decarboxylation is performed at low oxygen pressure, optionally with the addition of hydrogen peroxide, but without the addition of other organic additives such as e.g. anthraquinone derivatives or methylene blue. The process of the present invention can be performed without organic solvents and at high dry substance of the substrate while retaining the reaction specificity. Starting with glucose (anhydrous, monohydrate, high dextrose syrups), and/or fructose or invert sugar, the oxidative decarboxylation yields alkali metal arabinonate. Starting with galactose the product of the present process is lyxonate, and lactose hydrolysates give after the oxidative decarboxylation mixtures of lyxonate and arabinonate.

According to the present invention it is possible to apply low pressure of oxygen gas without adding anthraquinone derivatives or methylene blue, and without the use of organic solvents, and still obtain good reaction selectivity. Especially these anthraquinone derivatives are detrimental for the next reaction step in the present process, e.g. the hydrogenation of arabinonic acid to arabinitol in the presence of ruthenium based catalysts. The reaction in the presence of AMS requires an extensive working-up procedure to remove completely AMS from the substrate. FR 2 722 200 mentions the treatment with granular active carbon, but without explaining the procedure nor the obtained result. However, as shown in the examples of the present invention treatment only with active carbon is not sufficient to remove completely all traces of AMS. The complete removal of anthraquinone-2-sulphonic acid is required, because any trace of AMS poisons the ruthenium based catalyst, applied for the hydrogenation of arabinonic acid to arabinitol. It is therefore evident that the reaction as described in FR 2 722 200 is not feasible if the product is later to be hydrogenated in the presence of certain catalysts.

Several methods for removal of AMS from aqueous solutions have been described: J. Kiwi et. al New. J. Chem. 1993, 17 487–494 describe the heterogeneous photocatalytic degradation by means of titanium dioxide powder. In Applied Catalysis B: Environmental 1993 3 85–99 J. Kiwi et al. describe the homogeneous photocatalytic degradation by means of hydrogen peroxide and iron ions. 90% of the AMS is degraded in 3 hours but in total 15 hours are required for the complete removal. A. T. Hunter describes in J. Chromatogr. 1985 319 319–330 the separation of anthraquinone sulphonic acids using reversed phase HPLC in the presence of quaternary ammonium salts as ion-pairing agents. The ion pair interaction is demonstrated in the present invention as being sofar the best but cumbersome technique to remove all traces of anthraquinone-2-sulphonic acid.

The present invention discloses the production of arabinitol starting from glucose in a high yield while working at a pressure of between 0.5 to 10 bar preferably 1 to 6 bar, more preferably 2 to 5 bar without the addition of AMS and in the absence of organic solvents.

The reactions without the addition of AMS give products which can be worked up easily by crystallization of the alkali metal aldonate, and protonation with a known ion exchange treatment. To bring the reaction medium of the oxidative decarboxylation at the required alkaline pH, most commonly calcium hydroxide, potassium hydroxide or sodium hydroxide are used. Calcium hydroxide has already been described for this purpose and has the advantage of allowing easy crystallisation of the resulting calcium arabinonate, but it has the disadvantage of dosing in a practical way the calcium hydroxide to the reaction medium when applying low oxygen pressures. Potassium hydroxide or sodium hydroxide can easily be added to the reaction medium. The alkali metal arabinonates, such as potassium arabinonate and sodium arabinonate are crystallized from the reaction medium by adding methanol to the concentrated reaction medium. In the present invention potassium arabinonate can be crystallized from the reaction medium, after concentrating the mixture to high dry substance, but without adding additional methanol. To be able to crystallize sodium arabinonate in high crystalline yield, first an ion exchange treatment is required to bring the pH of the crude reaction medium from 13 to 8, preferably 7, such as has been described by J. Dubourg et. al Bull. Soc. Chim France 1959 1353–1362.

In the present invention the use of methanol is omitted.

The crystallization step which is optional is in fact a purification step to remove all traces of formiate, glycolate and eventually traces of erythronate present.

Since it is not possible to hydrogenate the aldonate salt, it has to be converted to the corresponding free acid or lactone. Several methods can be applied for this purpose, e.g. using concentrated sulphuric acid such as has been described in FR 2 722 200. However, the final product has to be free of any salt, since most common salts, organic and inorganic salts, are poisoning the hydrogenation catalyst. Traces of potassium perchlorate, potassium chloride, potassium sulphate and sodium acetate all have a retardation or inhibiting effect on the hydrogenation of aldonic acids. Other organic acids, such tartaric acid, lactic acid and malic acid all retard the respective hydrogenation reaction. Knowing this, the protonation of alkali metal aldonate to the corresponding aldonic acid is preferably done by applying strong ion exchange resins. Finally, the arabinonic acid is hydrogenated in the presence of ruthenium based catalysts.

The present invention is illustrated by a series of examples. The examples indicate that it is perfectly possible to perform the oxidative decarboxylation at low pressure and with high selectivity without the use of a redox catalyst such as AMS or added organic solvent.

Example 1 demonstrates that the combination of AMS and hydrogen peroxide can be replaced with oxygen and that when the reaction is performed at slightly elevated pressure the molar yield of the product is of the same order as when both AMS and hydrogen peroxide were used. Moreover it is shown that the reaction can be performed at high dry substance concentration. Preferably the reaction is performed at up to 10% dry substance, more preferably at up to 20 or even 30%. The advantage of the present process is however becoming more apparent if the catalytic hydrogenation step is considered.

Figure 2:
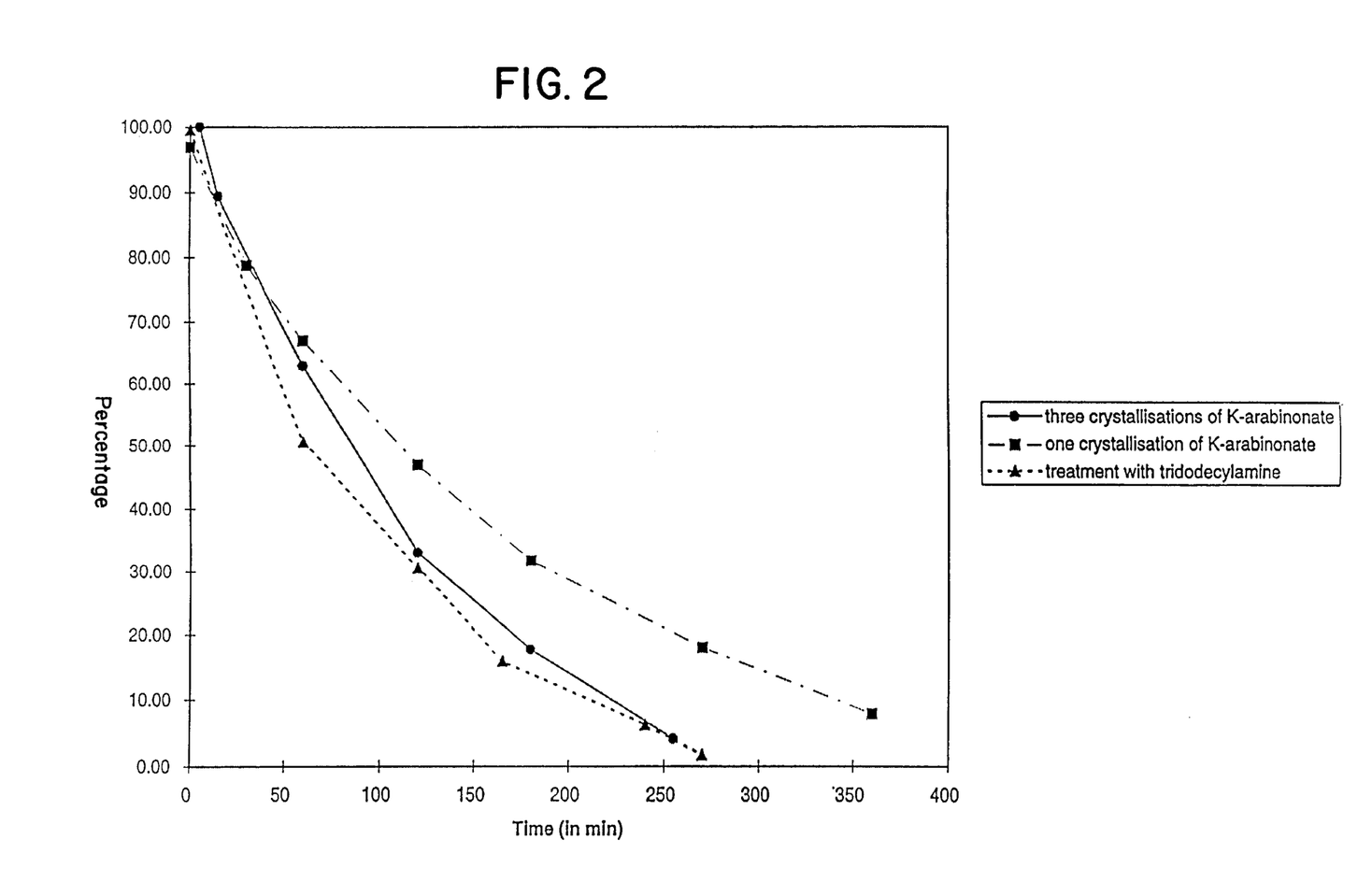
FIG. 2 shows the effect of substrate purity on aldonic acid hydrogenation.
Figure 3:
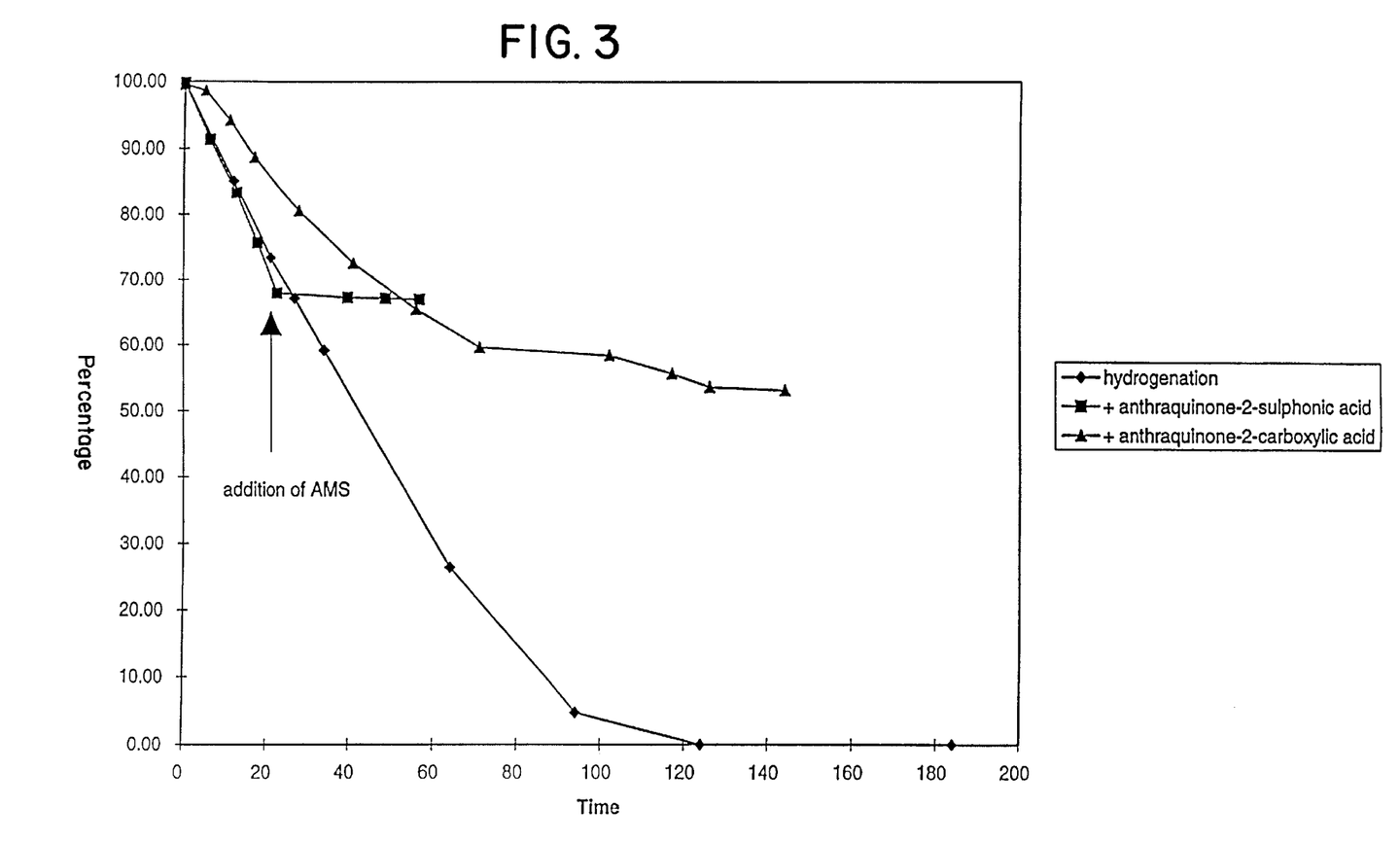
FIG. 3 shows the effect of the addition of AMS during aldonic acid hydrogenation.

Example 2 shows that extensive purification of the arabinonate is required in order not to influence the subsequent hydrogenation especially when AMS is used. FIG. 2 and subsequent figures show the decrease of the amount of arabinonic acid in time where the starting amount is put at 100%. FIG. 2 shows that the cleaner the arabinonic acid the faster the amount of arabinonic acid decreases. Thereby the yield is increased and the reaction time to completion is decreased. Repeated crystallization gives a product of a purity with good performance in hydrogenation. Treatment with tridodecylamine gives even better results as seen from FIG. 2. As a control experiment AMS was added to a hydrogenation mixture resulting in a clear inhibition of the reaction. (FIG. 3). Moreover, the presence of anthraquinone derivatives such as anthraquinone-2-sulphonic acid also inhibits the hydrogenation reaction. For comparative purpose it was tried to remove the AMS using active carbon. The result shows that it is very difficult to remove AMS in this way.

Example 3 demonstrates that using pure substrate the reaction temperature can be diminished from 150° to 135° C. At lower temperature the amount of cracking is lowered whereas the reaction time is not influenced to a large extent.

Finally it was shown that trace amounts of inorganic acids, or salts influence the hydrogenation reaction. The hydrogenation reaction is stimulated by addition of phosphoric or boric acid. (Example 4)

It can be concluded that the present invention fulfils all purity requirements to obtain good hydrogenation selectivity without catalyst poisoning.

The advantages of this process in comparison with earlier described processes such as part of the process disclosed in the international patent application WO 93/19030 are low processing costs, easy handling and easy working up of the reaction product due to the combination of the following steps:

1. an oxidative decarboxylation applying only low pressures of oxygen gas without the addition of anthraquinone derivatives nor the addition of organic solvents, optionally with the addition of hydrogen peroxide;
2. crystallization preferably from water without the addition of organic solvents;
3. protonation applying ion exchange resin to free the product of all traces of foreign ions;
4. hydrogenation in the presence of ruthenium based catalysts and obtain good selectivities, because of absence of poisoning impurities.

Figure 1:
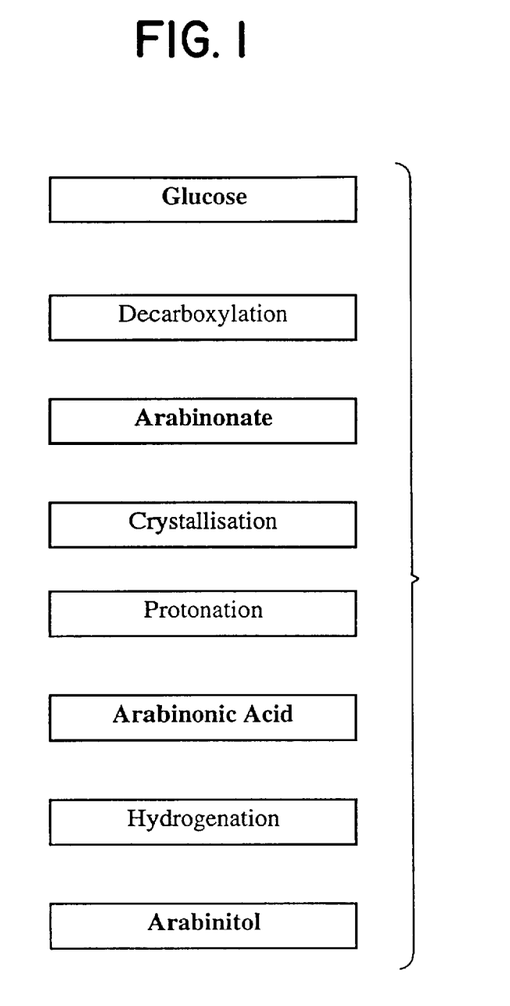
FIG. 1 shows a schematic presentation of the process of the present invention.

The process of the present invention is schematically shown in FIG. 1.

The invention is further illustrated by the following examples.

Example 1

Oxidative Decarboxylation

Oxidative Decarboxylation Applying Oxygen Gas at 2 Bar Pressure

A glucose solution (1.5 kg - 10% w/w solution) is heated to 45° C. in a two liter autoclave while stirring at 1000 rpm. The reactor containing the glucose solution is purged twice for 0.5 minutes with oxygen gas at 1 bar pressure. After purging, the oxygen pressure in the reactor is adjusted to 2 bar. The reaction is started by dosing the potassium hydroxide solution (242 g - 50% w/w solution) with a dosing burette to the glucose solution using a dosing speed of 1.3 mol KOH/h. The total dosing time required is 1.7 hours. The reaction mixture is stirred for a total reaction time of 5 hours, including the dosing time of the alkali. The product is determined by HPLC analysis. (see Table 1).

Comparative Example with the Use of AMS and Hydrogen Peroxide and Oxygen Gas at Atmospheric Pressure A glucose solution (1.5 kg - 10% w/w solution) is heated to 45° C. in a two liter batch reactor while stirring at 1000 rpm. During heating, the glucose solution is saturated with oxygen gas. Oxygen gas is bubbled through the reaction mixture at a flow rate of 0.2 l/min. The oxygen level in the solution is measured by means of an oxygen electrode. The anthraquinone-2-sulphonate (AMS - 2.25 g) and the hydrogen peroxide (0.78 g - 30% w/w solution) are dosed simultaneously to the glucose solution, before the addition of any alkali. The reaction is started by dosing the potassium hydroxide solution with a peristaltic pump to the glucose solution using a dosing speed of 0.9 mol KOH/h. The total alkali dosing time requires 2.8 hours. After alkali dosing, the reaction is continued until a colour change from red-brownish to white is observed, due to the redox reaction of the AMS catalyst. The total reaction time for glucose decarboxylation, including dosing time of alkali, is 5.5 hours. The product is determined by HPLC analysis. (see Table 1).

The procedure is repeated but oxygen gas is replaced by air at atmospheric pressure. The product is determined by HPLC analysis. (see Table 1).

Comparative Example with Oxygen Pressure of 2 Bar and Addition of AMS and Hydrogen Peroxide The procedure is similar to the first description, AMS and hydrogen peroxide are added simultaneously before purging with oxygen gas. The product is determined by HPLC analysis. (see Table 1).

Comparative Example with Oxygen Pressure of 2 Bar and Addition of Hydrogen Peroxide A starch hydrolysate solution, containing 95% glucose (30% w/w solution) is heated to 35° C. in a two liter autoclave while stirring at 1000 rpm. 0.2% hydrogen peroxide is added and the reactor containing the glucose solution is purged twice for 0.5 minutes with oxygen gas at 1 bar pressure. After purging, the oxygen pressure in the reactor is adjusted to 2 bar. The reaction is started by dosing the potassium hydroxide solution (50% w/w solution) with a dosing burette to the glucose solution using a dosing speed of 0.5 mol KOH/h. The total dosing time requires 8 hours. The product is determined by HPLC analysis. (see Table 1).

TABLE 1

| AMS | $H_2O_2$ | Molar yield arabinonate obtained with | | |
|---|---|---|---|---|
| | | $O_2$ atmospheric pressure | air atmospheric pressure | $O_2$ at 2 bar pressure |
| + | + | 93% | 80% | 94% |
| − | − | 55% | | 88% |
| − | + | | | 83% |

To demonstrate the applicability of this method even at higher dry substance, the first description, applying 2 bar oxygen pressure at 40° C. is followed for glucose solutions at 10%, 20% and 30% dry substance.

The glucose solution is heated to 40° C. in a two liter autoclave while stirring at 1000 ppm. The reactor containing the glucose solution is purged twice for 0.5 minutes with oxygen gas at 1 bar pressure. After purging, the oxygen pressure in the reactor is adjusted to 2 bar. The reaction is started by dosing the sodium hydroxide solution (45% w/w solution) with a dosing burette to the glucose solution using a dosing speed of 0.65 mol NaOH/h.

TABLE 2

| d.s. % | Molar yield arabinonate |
|---|---|
| 10% | 89% |
| 20% | 87% |
| 30% | 80% |

Example 2
Purification of Arabinonate (Obtained from Oxidative Decarboxylation in Presence of AMS), Followed by Protonation and Hydrogenation to Arabinitol
Crystallization Potassium arabinonate obtained according to Example 1 and in the presence of AMS is crystallised first from methanol/water. The crude reaction mixture (appr. 10% dry substance) is filtered over a paper filter in order to remove all insoluble AMS catalyst.

After filtration, the reaction medium is concentrated at 70° C. under reduced pressure until a concentration of 40% dry substance is obtained. The concentrated reaction mixture is precipitated in an equal weight of methanol. The precipitated potassium arabinonate is collected by filtration. The collected potassium arabinonate is washed twice with methanol and dried at room temperature.

These crystals have a purity of 96.9% (measured with HPLC-analysis). This purity is insufficient for the following hydrogenation step. (see FIG. 2 the substrate for the hydrogenation has been protonated by using Mitsubishi UBK 550 resin).
Recrystallization A 50% dry substance solution of methanol precipitated potassium arabinonate in water is prepared by heating the mixture to 95° C. The hot solution is filtered again to remove residual insoluble parts of AMS. The hot solution is slowly cooled down while stirring the solution. The potassium arabinonate crystals are collected by filtration. The crystals are dried at room temperature. (crop 1). The mother liquor is concentrated to 50% dry substance and a second crop of crystals is collected. (crop 2). Both crops are collected again to perform a second recrystallization applying the same conditions as for the first recrystallization. The purity of the collected crystals is 100%.

See FIG. 2 to observe the hydrogenation profile (the substrate for the hydrogenation has been protonated by using Mitsubishi UBK 550 resin). However, this product is not yet free from all traces of AMS, and AMS is detrimental for the catalyst. During one of the hydrogenation trials anthraquinone-2-sulphonate has been added to pure substrate to visualize the detrimental effect of AMS (FIG. 3).
Removal of Residual Anthraquinone-2-Sulphonic Acid by Ion-Pair Interaction The collected crystals with 100% purity, determined by HLPC-analysis, are protonated by using Mitsubishi UBK 550 resin.

To 200 g of 50% w/w solution of arabinonic acid, which contains traces of anthraquinone-2-sulphonic acid, 3.18 g tridodecylamine is added. Stir for 10 minutes at room temperature and add 2 g of active carbon. Stir the global solution for half an hour at 70° C. Cool down to room temperature and filtrate the solution over 0.45 μm filter.

This product is concentrated to be applied in the consecutive hydrogenation or it can be further concentrated to 70% dry substance to crystallize the corresponding arabinolactone.

This product is free of AMS and the profile of the hydrogenation shows the improvement compared with the substrate originating from three consecutive crystallizations as seen from FIG. 2.
Application of Active Carbon to Remove Anthraquinone-2-Sulphonic Acid Take the reaction mixture originating from an oxidative decarboxylation in presence of 0.2% AMS. The crude reaction mixture, at pH=12 (appr. 10% dry substance), is filtered over a paper filter in order to remove all insoluble AMS catalyst. Still 318 ppm AMS, which is photometrically determined at 330 nm, reside in the product. This product is treated with 0.5% active carbon and stirred for 1 h at 80° C. After filtration over 0.45 μm filter, still 48 ppm AMS remains in the product. As comparative trial the product containing 318 ppm AMS, is treated, at pH=12, with active carbon and tridodecylamine (see procedure above) and under these conditions, i.e. pH=12, the actual AMS content is reduced to 22 ppm. The treatment with tridodecylamine is twice as good as the treatment with active carbon solely.
Hydrogenation 110 g arabinonic acid is dissolved in 440 ml water, and is brought into a pressurized autoclave. 6% Ru(5%)/C is added to the solution and the reaction medium is heated to 150° C. The reaction is started by pressuring the autoclave with 40 bar hydrogen gas. The reaction is stopped 0.5 hour after complete hydrogen uptake is observed. In general the reaction is continued for 5 to 6 hours under the previously mentioned reaction conditions. (see Table 3)

Example 3
Purification of Arabinonate (Obtained from Oxidative Decarboxylation without AMS), Followed by Protonation and Hydrogenation to Arabinitol
Crystallisation Before crystallizing the alkali metal arabinonate (being sodium arabinonate or potassium arabinonate), the crude reaction mixture is brought to pH=7 with the aid of ion exchange resin (e.g. Lewatit S2528).

The resulting reacting mixture (pH=7) is concentrated under reduced pressure at 50° C. to 70% dry substance. The crystals are collected by filtration or centrifugation and are dried at room temperature. Sodium arabinonate is obtained in 95–97% purity and potassium arabinonate is obtained in 98–99% purity. The remaining impurities are glycolate and formiate.

Recrystallization

Figure 4:
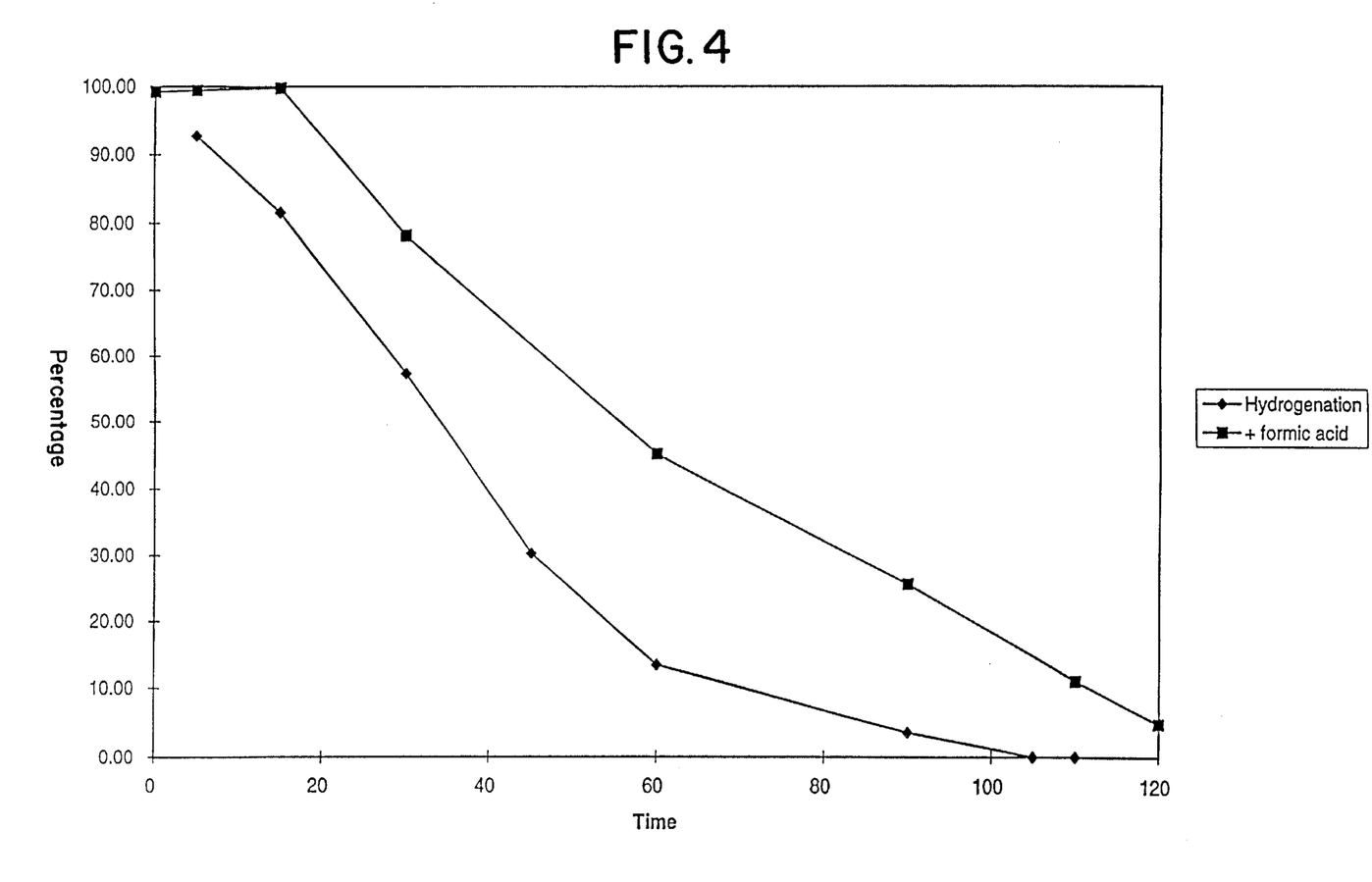
FIG. 4 shows the effect of formic acid on the aldonic acid hydrogenation.

The collected crystals are dissolved again in water to obtain a 70% solution. Cooling down to room temperature allows the crystallization of sodium arabinonate, obtained in 100% purity. This recrystallization is most of the time required to remove all traces of formiate. Complete removal is required because any trace of formic acid is poisoning the catalyst as seen from FIG. 4.

Hydrogenation

The thus obtained crystals are protonated by applying ion exchange resin (e.g. Lewatit S2528). 110 g arabinonic acid is dissolved in 440 ml water, and is brought into a pressurized autoclave. 6% Ru(5%)/C is added to the solution and the reaction medium is heated to 135° C. The reaction is started by pressuring the autoclave with 40 bar hydrogen gas. The reaction is stopped 0.5 hour after complete hydrogen uptake is observed. In general the reaction is continued for 6 hours under the previously mentioned reaction conditions. Using completely pure substrate the reaction temperature of the hydrogenation can be reduced from 150° C. to 135° C., while the reaction time is not elongated.

This reduction in reaction temperature has a significant effect on the cracking reactions occuring besides the hydrogenation of arabinonic acid (see Table 3). The reaction products are analysed by HPLC.

TABLE 3

| Source substrate* | Reaction Temp. | Reaction Time | Res. Acid | Pentitols | Cracking |
|---|---|---|---|---|---|
| + AMS | 130 | 1 h 30 | 20% | 69% | 11% |
| + AMS | 150 | 5 h 30 | 0% | 84% | 16% |
| − AMS | 150 | 5 h | 0% | 88% | 12% |
| − AMS | 140 | 5 h | 4% | 85% | 11% |
| − AMS | 135 | 6 h | 3% | 89% | 8% |
| − AMS | 130 | 7 h | 3% | 90% | 7% |
| − AMS | 125 | 10 h | 2% | 92% | 6% |

*describes where the substrate is originating from: oxidative decarboxylation reaction with or without anthraquinone-2-sulphonic acid (AMS).

Example 4

Protonation with Ion Exchange Resin

The protonation of alkali metal arabinonate to arabinonic acid is preferably performed with ion exchange resin (e.g. Mitsubishi UBK 550, Lewatit S2528).

After protonation with common inorganic acids (e.g. sulphuric acid, hydrochloric acid, perchloric acid) traces of inorganic salts are remaining in the substrate for hydrogenation and are inhibiting the hydrogenation catalyst. The protonation is also not feasible with the aid of organic acids, because most of them are poisoning the hydrogenation catalyst.

Figure 5:
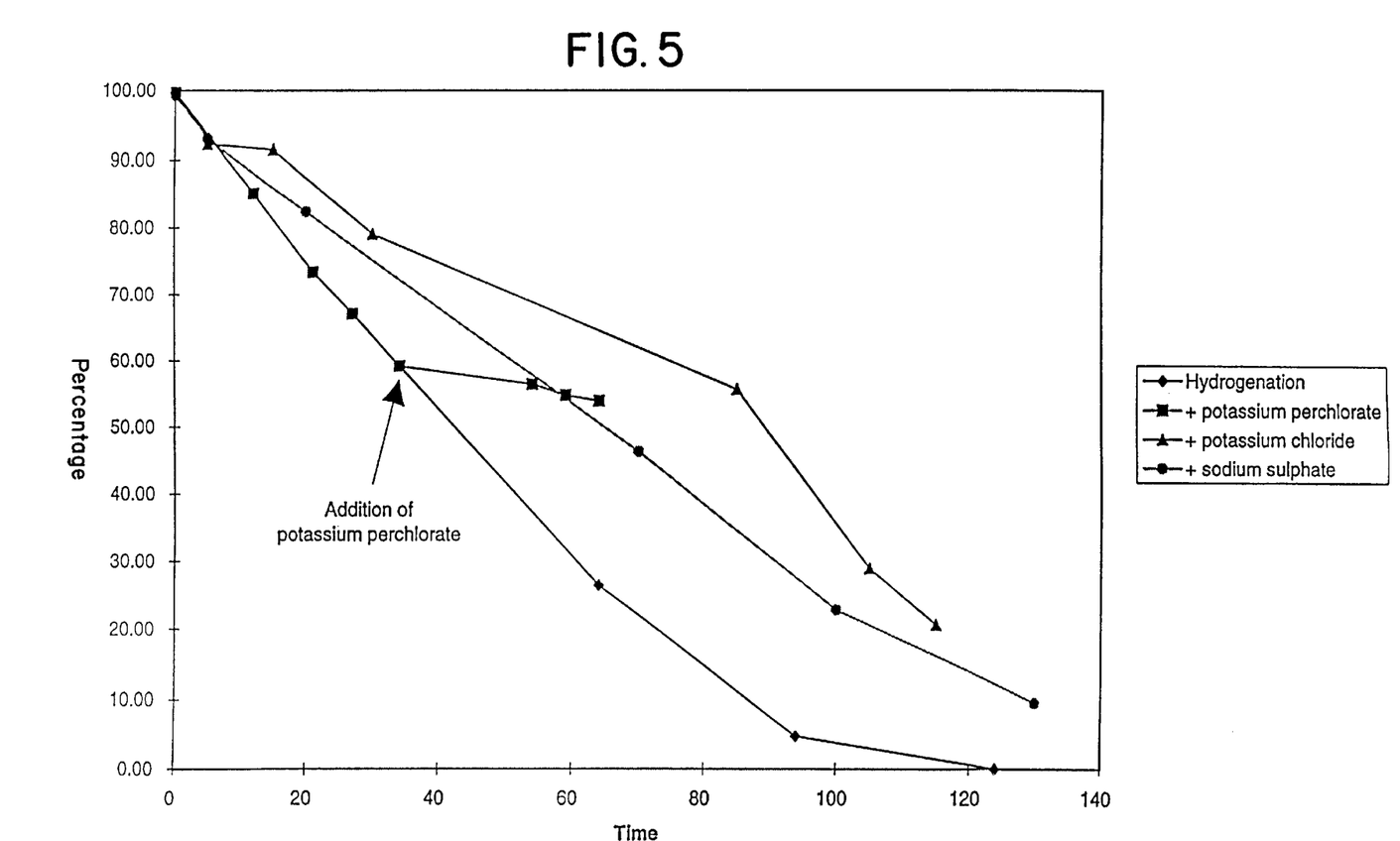
FIGS. 5 and 6 show the effect of residual inorganic salts and organic salts and acids on the aldonic acid hydrogenation.
Figure 6:
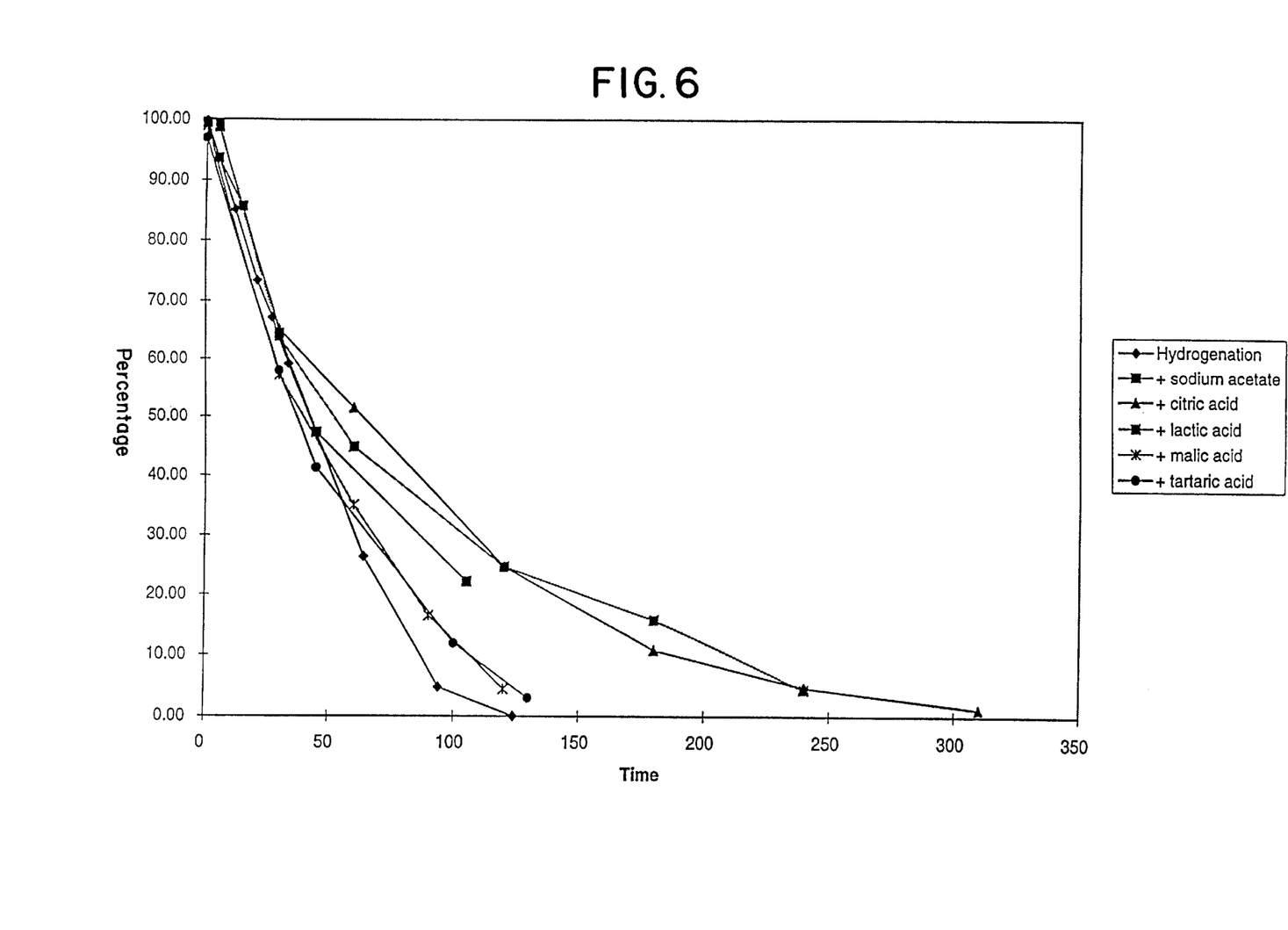
Figure 7:
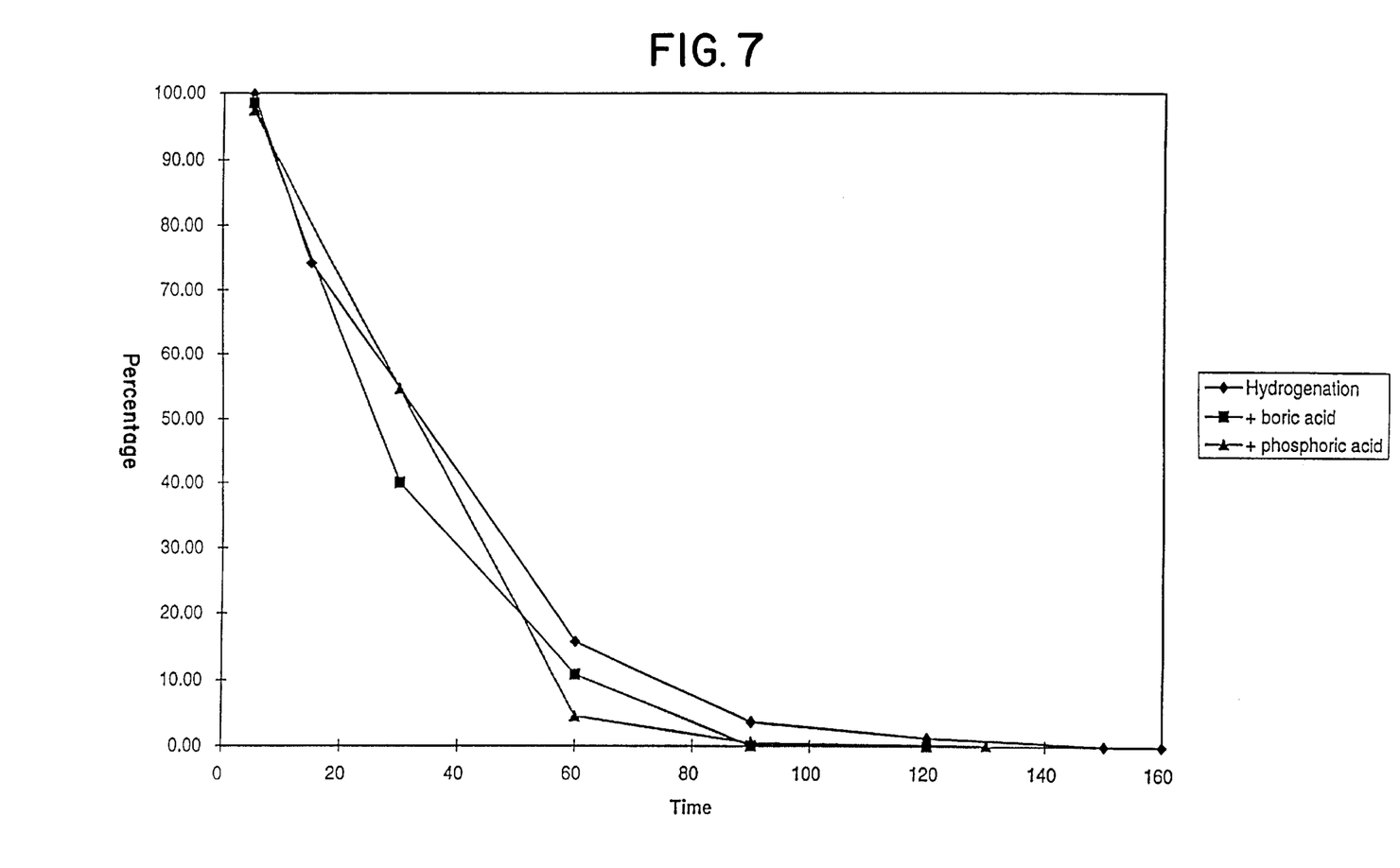
FIG. 7 shows the positive effect of phosphoric acid and boric acid on the hydrogenation.

The ruthenium based catalysts, applied for this hydrogenation are sensitive towards any trace of any salt, see FIGS. 5 & 6. The ruthenium based catalyst is promoted by the addition of phosphoric acid or boric acid (FIG. 7).

What we claim is:

1. A method for producing arabinitol from glucose (anhydrous, monohydrate, high dextrose syrups (starch hydrolysates)) and/or fructose, and/or galactose, or lactose hydrolysates, or invert sugar, said method comprising the following steps:

a) oxidatively decarboxylating a hexose to yield mainly $C_5$-aldonate alkali metal salts, wherein step a) is conducted in the presence of oxygen at a low pressure of 1 to 6 bar while adding neither anthraquinone derivatives nor organic solvents and optionally with addition of hydrogen peroxide, b) crystallizing the obtained $C_5$-aldonate alkali metal salts, c) protonating the $C_5$-aldonate alkali metal salts to their corresponding free aldonic acid, d) optionally crystallizing the intermediate aldonolactone, and e) hydrogenating aldonic acid to arabinitol.

2. The method according to claim 1, wherein the oxygen pressure is between 2 to 5 bar.

3. The method according to claim 1, wherein step b) is performed directly from water or from water/alcohol mixtures.

4. The method according to claim 1, wherein step c) is performed by using ion exchange resins.

5. The method according to claim 1, wherein step e) is performed in the presence of a ruthenium based hydrogenation catalyst.

6. The method according to claim 5, wherein the hydrogenation is conducted at a temperature between 100° and 170° C.

7. The method according to claim 5 or 6, wherein the hydrogenation is promoted by the addition of at least one of phosphoric acid or boric acid.

8. The method according to claim 1, wherein step b) is performed directly from water.

9. The method according to claim 1, wherein step c) is performed using a strong ion exchange resin.

10. The method according to claim 8, wherein step e) is performed in the presence of a ruthenium based hydrogenation catalyst.

11. The method according to claim 5 or 10, wherein the hydrogenation is conducted at a temperature between 110° C. and 150° C.

12. The method according to claim 5 or 10, wherein the hydrogenation is conducted at a temperature between 120° C. and 140° C.

13. The method according to claim 11 or 12, wherein the hydrogenation step is promoted by the addition of at least one acid comprising phosphoric acid or boric acid.

14. The method according to claim 1, wherein step a) oxygen is used at a pressure between 2 to 5 bars;

step b) is performed directly from water or from a water/alcohol mixture;

step c) is performed using a strong ion exchange resins; and step e) is performed in the presence of a hydrogenation catalyst at a temperature between 100° C. and 170° C., and said hydrogenation is promoted by the addition of at least one acid selected from the group consisting of phosphoric and boric acid.

15. A method according to claim 4 wherein the ion exchange resins comprise strong ion exchange resins.

* * * * *